United States Patent
Zlicar (12)

(10) Patent No.: US 6,384,238 B1
(45) Date of Patent: May 7, 2002

(54) PROCESS FOR THE PREPARATION OF SIMVASTATIN AND ANALOGS THEREOF

(75) Inventor: Marco Zlicar, Celje (SI)

(73) Assignee: Lek Pharmaceutical and Chemical Company d.d., Ljubljana (SI)

( * ) Notice: Subject to any disclaimer, the term of this patent is extended or adjusted under 35 U.S.C. 154(b) by 0 days.

(21) Appl. No.: 09/857,100

(22) PCT Filed: Dec. 1, 1999

(86) PCT No.: PCT/IB99/01912

§ 371 Date: May 31, 2001

§ 102(e) Date: May 31, 2001

(87) PCT Pub. No.: WO00/32585

PCT Pub. Date: Jun. 8, 2000

(30) Foreign Application Priority Data

Dec. 2, 1998 (SI) .............................................. P-9800300

(51) Int. Cl.[7] .......................... C07F 7/02; C07D 309/30
(52) U.S. Cl. ........................................ 549/214; 549/292
(58) Field of Search ................................ 549/292, 214

(56) References Cited

U.S. PATENT DOCUMENTS

| 4,444,784 A | 4/1984 | Hoffman et al. ............ 424/279 |
| 4,582,915 A | 4/1986 | Sleteinger et al. ........... 549/292 |
| 4,820,850 A | 4/1989 | Verhoeven et al. .......... 549/292 |
| 5,159,104 A | 10/1992 | Dabora et al. ............... 560/119 |

FOREIGN PATENT DOCUMENTS

| EP | 0 287 340 A2 | 10/1988 |
| WO | WO 98/12188 | 3/1998 |
| WO | WO 99/43665 | 9/1999 |

OTHER PUBLICATIONS

Askin, et al., "Synthesis of Synvinolin: Extremely High Conversion Alkylation of an Ester Enolate," J. Org. Chem. 56, 4929–4932 (1991).

*Primary Examiner*—Amelia Owens
(74) *Attorney, Agent, or Firm*—Bromberg & Sunstein LLP

(57) ABSTRACT

Lovastatin, pravastatin, simvastatin, mevastatin, derivatives and analogs thereof are known as HMG-CoA reductase inhibitors and are used as antihypercholesterolemic agents. The majority of them are produced by fermentation using microorganisms of different species identified as species belonging to Aspergillus, Monascus, Nocardia, Amycolatopsis, Mucor or Penicillium genus, and some are obtained by treating the fermentation products using the methods of chemical synthesis for example simvastatin. This invention relates to the novel method for the acylation of sterically hindered alcohols which is applicable in the process for the preparation of simvastatin and derivatives thereof.

10 Claims, No Drawings

PROCESS FOR THE PREPARATION OF SIMVASTATIN AND ANALOGS THEREOF

FIELD OF THE INVENTION

This invention relates to a novel process for the acylation of sterically hindered alcohols which is one of the crucial steps in the process for the preparation of simvastatin and derivatives thereof as well as other related HMG-CoA reductase inhibitors. More particularly, this invention relates to a novel acylation process which is applicable in the preparation of simvastatin and derivatives thereof from alcohols of formula I (R representing a protective group).

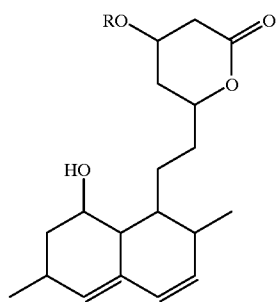

I

BACKGROUND OF THE INVENTION

Lovastatin, pravastatin, simvastatin, mevastatin, atorvastatin, derivatives and analogs thereof are known as HMG-CoA reductase inhibitors and are used as antihypercholesterolemic agents. The majority of them are produced by fermentation using microorganisms of different species identified as species belonging to Aspergillus, Monascus, Nocardia, Amycolatopsis, Mucor or Penicillium genus, some are obtained by treating the fermentation products using the methods of chemical synthesis (simvastatin) or they are the products of total chemical synthesis.

In the literature several processes for the preparation of simvastatin are known which are mainly based on one of the two following basic principles.

A process of direct methylation of the 2-(S)-methylbutyryloxy side chain of lovastatin is disclosed in U.S. Pat. No. 4,582,915. That process is based on direct methylation of the 2-(S)-methylbutyryloxy side chain of lovastatin using a methyl alkyl amide and a methyl halide in a single step. The described process has certain disadvantages: the low level of conversion in the C-methylation step, low temperatures (−70 to −15° C.) required for the reaction to be carried out and a number of undesired side reactions of methylation occurring at other sites of the molecule as well as using of butyl lithium which produces an explosive reaction with water and is highly pyrogen at higher concentrations. With minor modifications the yields in the methylation step may be improved, however, the total yields remain relatively low. U.S. Pat. No. 4,820,850 discloses a process for methylation of the 2-(S)-methylbutyrylox side chain of lovastatin using a single charge of amide base and alkyl halide. The process disclosed therein involves six steps; despite the fact that the level of conversion is high in the methylation step, the process is not economical.

The second basic principle is de-esterification of the 2-methylbutyrate side chain of lovastatin and re-esterification wherein the desired 2,2-dimethylbutyrate (simvastatin) is formed. U.S. Pat. No. 4,444,784 discloses a process which comprises de-esterification of the 2-methylbutyrate side chain of lovastatin, protection of the 4-hydroxy group on the pyranone ring with t-butyldimethylchlorosilane, re-esterification with 2,2-dimethylbutyryl chloride and deprotection of the 4-hydroxy group. The reaction of re-esterification as described in the example is however very slow and requires 18 to 36 hours and a high temperature of 100° C., and the yields are very low. In addition, the reaction leads to a number of side products which are formed during the reaction since a protecting group is easily eliminated under these rigid conditions. Apart from side products, unconverted starting materials additionally complicate the isolation of pure simvastatin and lower the yield of the disclosed process.

EP 0 287 340 discloses an improvement of the acylation step in the above process which involves the addition of alkali metal bromides under the presence of dialkylaminopyridine as a catalyst in a solvent, preferably pyridine. The presumed mechanism of reaction is characterized by in situ generated reactive acylated intermediates such as the acyl bromides (a), a pyridinium complex (h) or a dialkylaminopyridinium complex (c), wherein X is a chloride ion or bromide ion. The reaction times are shorter (6 to 8 hours), and the temperatures required are much lower (from 25 to 75° C.).

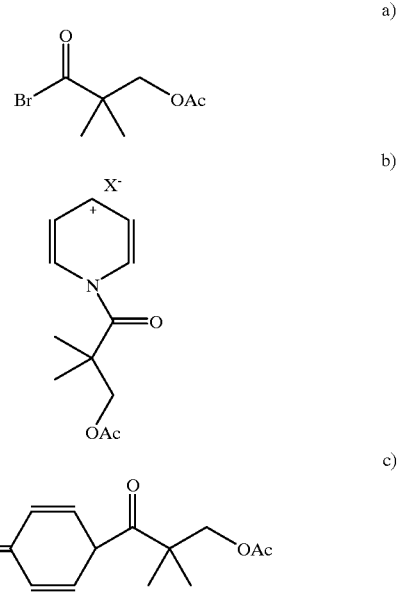

SUMMARY OF THE INVENTION

It is an object of the present invention to provide a novel improved method for the acylation of sterically hindered alcohols which is applicable in the process for the preparation of simvastatin and derivatives thereof as well as other related HMG-CoA reductase inhibitors and exerts an excellent yield, is cheaper, less toxic and shows less side reactions.

This is accomplished by the present invention.

According to the present invention, there is provided a process for the preparation of compounds of formula

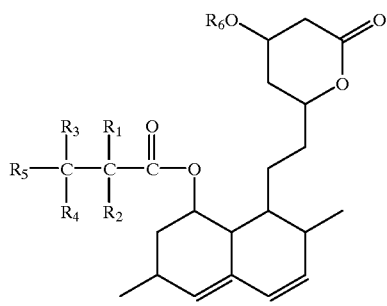

wherein $R_1$ and $R_2$ are independently hydrogen or alkyl with one to ten C atoms, $R_3$ and $R_4$ are independently hydrogen or alkyl with one to three C atoms, $R_5$ is hydrogen, halogen or alkyl with one to three C atoms, $R_6$ is a protecting group; which comprises combining of acyl chlorides of the formula

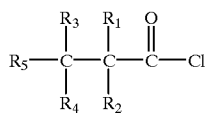

in the presence of a halide of the formula $KX_n$ in which K is Li, Mg, Ca, Zn, Fe, Ni or Al and X is Cl or Br, and n is 1, 2 or 3 (depending on the cation charge of K) with an alcohol of formula

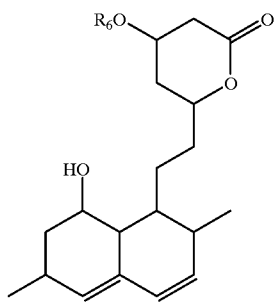

in an organic solvent in the absence of dialkylaminopyridine as a catalyst to yield a compound of formula:

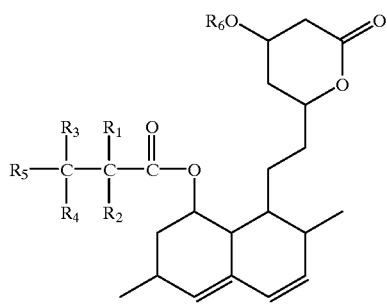

DESCRIPTION OF THE INVENTION

In our developmental and research work, contrary to the statements in EP 0 287 340, we have surprisingly found the following:

Acylation reactions are accomplished equally well with LiCl and LiBr; in case the former is used slightly higher temperature (80 to 95° C.) is required for the equivalent effectiveness.

Acylation reactions with NaBr and KBr are carried out much slower and with more side effects than with LiBr and LiCl.

Acylation reactions are also successfully carried out with other suitable metal halides. $MgBr_2$ and $MgCl_2$ are effective wherein under the same conditions the reactions with $MgBr_2$ proceed slightly faster than with $MgCl_2$. $MgCl_2$ catalyses slightly slower than LiCl. $MgBr_2$ and LiBr are approximately comparable by the reaction rate. Similar reactivity has been observed when $ZnBr_2$ and $ZnCl_2$ are used. The results were very good with $NiCl_2$ and $FeCl_2$. The use of $AlCl_3$ and especially of $BF_3$ showed the tendency of a formation of impurities.

The rate of acylation reaction and its effectiveness remain almost unchanged if a catalyst from the group of N,N-dialkylaminopyridines or the group of cycloalkylated aminopyridines is not added as disclosed in EP 0 287 340. If any of the above chlorides (Mg, Zn, Li) is used without addition of the catalyst, the intermediate (c), as disclosed in EP 0 237 340, is not generated and the reaction is carried oat equally successfully as in the examples described in this invention. Regarding the statements from the cited patent, the conclusion may be drawn that the acylation reaction would proceed slower than that described in U.S. Pat. No. 4,444,784 wherein the catalyst from the group of N,N-dialkylaminopyridines or cycloalkylated aminopyridines was not added.

As it is evident from EP 0 287 384, in situ generated reactive acyl bromides (a) being more reactive than acyl chlorides, and reactive acylated intermediates (b) and (c) are responsible for acceleration of the acylation reaction. However, the results of our experiments suggest that the, progress of the reaction depends on the cation in the halide added as a catalyst rather than on the bromide ion from the alkali metal bromide and in situ generated more reactive acyl bromides. We have also found that the progress of the reaction primarily depends on the size of cation, positive charge per cation area unit and on its ability for complexing with the carbonyl group in the acyl chloride. The cation site is important primarily because it may be sterically hindered during the generation of reactive intermediate II (only sufficiently small cations are capable of generating reactive acylated intermediates), and the reactivity of generated acylated intermediate II depends on charge and the ability of complexing with the carbonyl group.

II

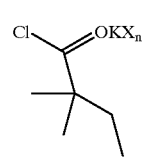

X may denote Cl or Br

K may denote Li, Mg, Ca, Zn, Fe, Ni or Al n may denote 1, 2 or 3 depending on cation charge The molecule $KX_n$ is approached to the carbonyl group of acyl chloride and attached to the oxygen atom thus inducing shifts in the arrangement of electrons in the molecular orbitals in the carbonyl group affords easier elimination of the chloride atom from the acyl chloride molecule. This leads to acceleration of the acylation reaction. Used acyl chloride may be selected from the compounds of formula III depending on the desired final product.

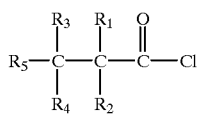
III wherein
$R_1$ and $R_2$ are independently hydrogen or alkyl with one to ten C atoms; $R_3$ and $R_4$ are independently hydrogen or alkyl with one to three C atoms; $R_5$ is hydrogen, halogen or alkyl with one to three C atoms.

The instant method is advantageous, inter alia, because it avoids the use of toxic N,N'-dialkylaminopyridines and cycloalkylated aminopyridines. Further, chlorides are used preferably instead of bromides. Since a bromide ion is much more sensitive when exposed to atmosphere and other oxidants than a chloride ion, for example, usage of LiCl decreases the risk of product contamination due to possible oxidation. Therefore the reaction mixtures with lithium chlorides are less coloured than those with the lithium bromide. Regarding the fact that it is difficult to eliminate the products of undesired side reactions, only use of appropriate chlorides remarkable facilitates the isolation of the desired final products. In addition to the above, a bromide ion itself is more toxic than a chloride ion. As a result, the process according to the present invention tends to show less side products as the acylated intermediate (c) disclosed EP 0 287 384 is not generated due to the absence of dialkylaminopyridines as a catalyst.

In the acylation process of sterically hindered alcohols, that is the process of the present invention, an appropriate metal chloride or bromide, preferably a metal chloride or a divalent metal bromide of Li, Mg, Ca, Zn, Fe or Ni, more preferably a metal chloride and particularly LiCl, and an acyl chloride, are dissolved in an appropriate solvent, such as pyridine, collidine, lutidine, picoline and acetonitiile, dioxane, tetrahydrofurane, N,N-dimethylformamide and a mixture of pyridine and tetrahydiofurane, preferably in pyridine.

A suitable reaction is carried out as follows: To the reaction mixture, an alcohol of the formula I is added and the resulting mixture is agitated under a nitrogen atmosphere in an oil bath at a temperature between 75 and 110° C., preferably between 75° and 95° C. The progress of the reaction is monitored by HPLC and the reaction is discontinued when the assay of the starting alcohol is less than 2%. The reaction is carried out from 3 to 10 hours. After completed reaction, the solvent is evaporated in vacuo on a rotary evaporator, and distilled water and dichloromethane are added to the residue and extracted. In place of dichloromethane, any other organic solvent which is poorly miscible or soluble in water may be used. The dichloromethane extract is separated and washed with an aqueous sulphuric acid solution or any other inorganic acid such as phosphoric acid and hydrochloric acid, with water and then with an aqueous $NaHCO_3$ solution. Dichloromethane is then evaporated on a rotary evaporator, and the crude product can be used directly in the next reaction. For obtaining simvastatin or derivatives or analogs thereof, the protecting group R can be removed by deprotecting reactions known to those skilled in the art.

The sequence below displays an entire route for the preparation of simvastatin and derivatives thereof using the acylation process of the instant invention:

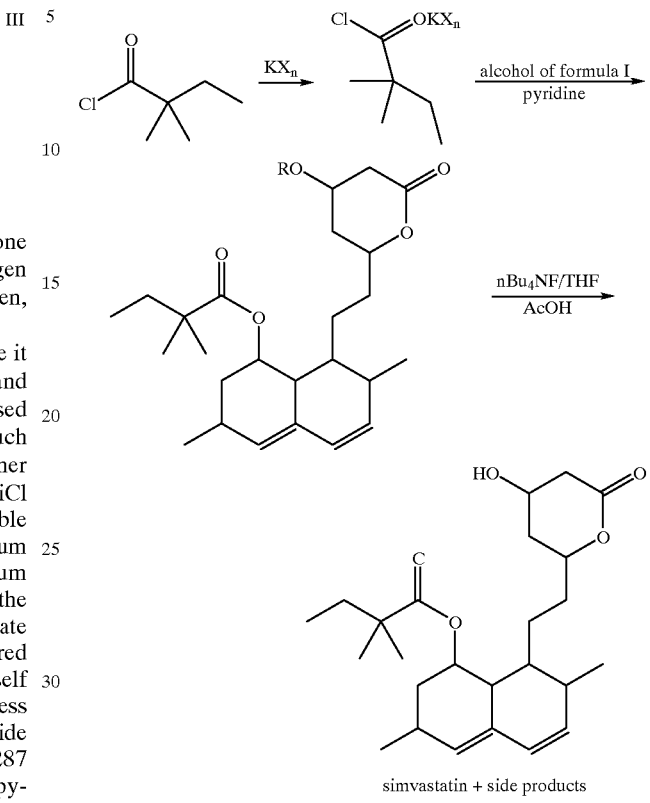

simvastatin + side products

A suitable and preferred protecting group $R_6$ used in the present invention is t-BuMe$_2$Si.

According to a preferred embodiment of the present invention, the compound prepared is 6(R)-[2-(8'(S)-2",2"-dimethylbutyryloxy-2'(S),6'(R)-dimethyl-1',2',6',7',8',8a-(R)-hexahydronaphthyl-1'(S))ethyl]-4(R)(dimethyl-tercbutylsiloxy)-3,4,5,6-tetrahydro-2H-pyran-2-one.

The present invention is illustrated but in no way limited by the following examples.

EXAMPLES

Example 1
Preparation of 6(R)-[2-(8'(S)-2",2"-dimethylbutyryloxy-2'(S),6'(R)-dimethyl-1',2',6',7',8',8a-(R)-hexahydronaphthyl-1'(S)) ethyl]-4(R)(dimethyl-terc-butylsiloxy)-3,4,5,6-tetrahydro-2H-pyran-2-one with LiBr as a catalyst 1 g of LiBr and 2 ml of 2,2-dimethylbutaniol chloride were dissolved in 20 ml of pyridine. 2 g of 6(R)-[2-(8'(S)-hydroxy-2'(S),6'(R)-dimethyl-1',2',6',7',8',8a-(R)-hexahydronaphthyl-1'(S))ethyl]4(R)(dimethyl-terc-butylsiloxy)-3,4,5,6-tetrahydro-2H-pyran-2-one (hereinafter Si-lactone) was added and the mixture was agitated in an oil-bath at a temperature between 75 and 80° C. under a nitrogen atmosphere. The progress of the reaction was monitored by BPLC analytical method and the reaction was discontinued when the assay of the starting Si-lactone was less than 2%. Pyridine was evaporated in vacuo on a rotary evaporator, and 20 ml of demineralized water and 30 ml of dichloromethane were added to the residue and extracted. The aqueous phase was discarded, the dichloromethane phase was further washed with 30 ml of 3% aqueous sulphuric acid solution, 30 ml of water and then with 20 ml of 5% aqueous NaHCO$_3$ solution. Dichloromethane was evaporated on a rotary evaporator to give 3 g of the crude product 6(R)-[2-8'(S)-2",2"-dimethylbutyryloxy-2'(S),6'(R)-dimethyl-1',2',6',7',8',8a-(R)hexahydronaphthyl-1'(S))ethyl]-4(R)(dimethyl-terc-butylsiloxy)-3,4,5,6-tetrahydro-2H-pyran-2-one in the form of oil which can be used directly in the next step of the preparation of simvastatin. 2",2"-dimethylbutyryloxy-2'(S),6'(R)-dimethyl-1',2',6',7',8',8a-(R)hexahydronaphthyl-1'(S))ethyl]-4(R)(dimethyl-terc-butylsiloxy)-3,4,5,6-tetrahydro-2H-pyran-2-one in the form of oil which can be used directly in the nest step of the preparation of simvastatin.

Example 2

Preparation of 6(R)-[2-(8'(S)-2",2"-dimethylbutyryloxy-2'(S),6'(R)-dimethyl-1',2',6',7',8',8a-(R)-hexahydronaphthyl-1'(S))ethyl]-4(R)(dimethyl-terc-butylsiloxy)-3,4,5,6-tetrahydro-2H-pyran-2-one with LiCl as a catalyst 1 g of LiCl and 2 ml of 2,2-dimethylbutaniol chloride were dissolved in 20 ml of pyridine. 2 g of Si-lactone was added and the mixture was agitated in an oil-bath at a temperature between 85 and 90° C. under a nitrogen atmosphere. The progress of the reaction was monitored by EPLC analytical method and the reaction was discontinued when the assay of the starting Si-lactone was less that 2%. Pyridine was evaporated in vacuo on a rotary evaporator, and 20 ml of demineralized water and 30 ml of dichloromethane were added to the residue and extracted. The aqueous phase was discarded, the dichloromethane phase was further washed with 30 ml of 3% aqueous sulphuric acid solution, 30 ml of water and then with 20 ml of 5% aqueous NaHCO$_3$ solution. Dichloromethane was evaporated on a rotary evaporator to give 3 g of the crude product 6(R)-[2-(8'(S)2",2"-dimethylbutyryloxy-2'(S),6'(R)dimethyl-1',2',6',7',8',8a-(R)-hexahydronaphthyl-1'(S))ethyl]-4(R)(dimethyl-terc-butylsiloxy)-3,4,5,6-tetrahydro-2H-pyran-2-one in the form of oil which can be used directly in the next step of the preparation of simvastatin.

Example 3

Preparation of 6(R)-[2-(8'(S)-2',2"-dimethylbutyryloxy-2'(S),6'(R)-dimethyl-1',2',6',7',8',8a-(R)-hexahydronaphthyl-1'(S))ethyl]-4(R)(dimethyl-terc-butylsiloxy)-3,4,5,6-tetrahydro-2H-pyran-2-one with MgBr$_2$ as a catalyst.

0.5 g of MgBr$_2$ and 1 ml of 2,2-dimethylbutanoil chloride were dissolved in 9 ml of pyridine. 1 g of Si-lactone was added and the mixture was stirred in an oil-bath at a temperature between 75 and 80° C. under a nitrogen atmosphere. The progress of the reaction was monitored by HPLC and TLC analytical methods which showed that the reaction was completed in after three hours. The isolation of the crude product 6(R)-[2-(8'(S)-2",2"-dimethylbutyryloxy-2'(S), 6(R)-dimethyl-1',2',6',7',8',8a-(R)-hexahydronaphthyl-1'(S))ethyl]-4(R)(dimethyl-terc-butylsiloxy)-3,4,5,6-tetrahydro-2H-pyran-2-one in the form of oil was effected by the process disclosed in Example 1. The obtained crude product can be used directly in the next step of the preparation of simvastatin.

Example 4

Preparation of 6(R)-[2-(8'(S)-2",2"-dimethylbutyryloxy-2'(S),6'(R)-dimethyl-1',2',6',7',8',8a-(R)-hexahydro-naphthyl-1'(S))ethyl]-4(R)(dimethyl-terc-butylsiloxy)-3,4,5,6-tetrahydro-2H-pyran-2-one with different halides as catalysts The process for preparation of the crude product 6(R)-[2-(8'(S)-2",2"-dimethylbutyryloxy-2'(S),6'(R)-dimethyl-1', 2',6',7',8',8a-(R)-hexahydronaphthyl-1'(S))ethyl]-4(R)(dimethyl-terc-butylsiloxy)-3,4,5,6-tetra-hydro-2H-pyran-2-one disclosed in Example 3 was repeated with other halides, listed in the table below. The amounts of the reactants, reaction conditions and duration of the reaction are also shown in the same table.

| Example | Halide | Si-lactone | 2,2 dimethyl butanoil chloride | Pyridine | Temperature | End of reaction |
|---|---|---|---|---|---|---|
| 4 | MgCl$_2$ 0.6 g | 1 g | 1.2 ml | 9 ml | 90–95° C. | after 7 hours |
| 5 | CaBr$_2$ 0.5 g | 1 g | 1 ml | 9 ml | 75–85° C. | after 4 hours |
| 6 | CaCl$_2$ 0.5 g | 1 g | 1 ml | 10 ml | 90–95° C. | after 4 hours* |
| 7 | ZnBr$_2$ 0.5 g | 0.5 g | 0.4 ml | 4 ml | 75–85° C. | after 3 3/4 hours |
| 8 | ZnCl$_2$ 0.5 g | 1 g | 1 ml | 1 ml | 85–90° C. | after 10 hours |

*after 4 hours the reaction was discontinued, the assay of the acylated product according to HPLC was 33%.

Example 5

Preparation of 6(R)-[2-(8'(S)-2",2"-dimethylbutyryloxy-2'(S),6'(Z)-dimethyl-1',2',6',7',8',8a-(R)-hexahydro-naphthyl-1'(S)) ethyl]-4(R)(dimethyl-terc-butylsiloxy)-3,4,5,6-tetrahydro-2H-pyran-2-one with further halides as catalysts 2 g of 6(R)-(2-(8'(S)-hydroxy-2'(S),6'(R)-dimethyl-1',2', 6',7',8',8a-(R)-hexahydronaphthyl-1'(S))ethyl]-4(R)(dimethyl-terc-butylsiloxy)-3,4,5,6-tetrahydro-2H-pyran-2-one -(Si-lactone), 2 ml of 2,2-dimethylbutanoyl chloride and 0.8 g of the catalyst (BF$_3$, AlCl$_3$, FeCl$_3$ or NiCl$_2$) were dissolved in 20 ml of pyridine and the mixture was stirred in an oil-bath at a temperature of 95° C. under a nitrogen atmosphere for 6 hours. The progress of the reaction was measured by HPLC. After the reaction was finished, the pyridine was evaporated in vacuo on a rotary evaporator, and 20 ml of demineralized water and 30 ml of dichloromethane were added to the residue and extracted. The aqueous phase was discarded, the dichloromethane phase was further washed with 30 ml of 3% aqueous sulphuric acid solution, 30 ml of water and then with 20 ml of 5% aqueous NaHCO$_3$ solution. Dichloromethane was evaporated on a rotary evaporator in the form of oil which can be used directly in the next step of the preparation of simvastatin. atmosphere for 6 hours, The progress of the reaction was measured by, HPLC. After the reaction was finished, the pyridine was evaporated in vacuo on a rotary evaporator, and 20 ml of demi water and 30 ml of dichloromethane were added to the residue and extracted. The aqueous phase was discarded, the dichloromethane phase was further washed with 30 ml of 3% aqueous sulphuric acid solution, 30 ml of water and then with 20% of 5% aqueous NaHCO$_3$ solution. Dichloromethane was evaporated on a rotary in the form of oil which can be used directly in the next step of the preparation of simvastatin.

What is claimed is:

1. A process for the preparation of compounds of formula

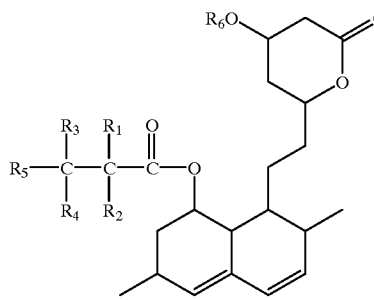

wherein $R_1$ and $R_2$ are independently hydrogen or alkyl with one to three C atoms, $R_3$ and $R_4$ are independently hydrogen or alkyl with one to three C atoms, $R_5$ is hydrogen, halogen or alkyl with one to three C atoms, $R_6$ is a protecting group; which comprises combining of acyl chlorides of the formula

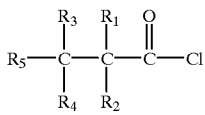

in the presence of a halide of the formula $KX_n$ in which K is Li, Mg, Ca, Zn, Fe or Ni and X is Cl or Br, and n is 1, 2, or 3, depending on the cation charge of K, with an alcohol of formula

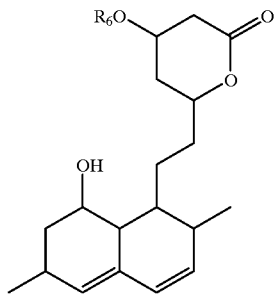

in an organic solvent in the absence of dialkylaminopyridine as a catalyst to yield a compound of formula:

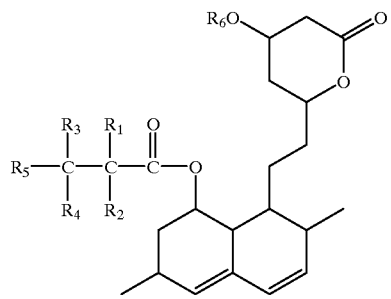

2. A process of claim 1 wherein the compound prepared is 6(R)-[2-(8'(S)-2'',2''-dimethylbutyryloxy-2'(S),6'(R)-dimethyl-1',2',6',7',8',8a-(R)-hexahydronaphthyl-1'(S))ethyl]-4(R)(dimethyl-terc-butylsiloxy)-3,4,5,6-tetrahydro-2H-pyran-2-one.

3. A process according to claim 1 wherein chlorides of Li, Mg, Ca, Zn, Fe or Ni are used as halide of formula $KX_n$.

4. A process according to claim 3 wherein lithium chloride is used as halide of formula $KX_n$.

5. A process according to claim 1 wherein the organic solvent is selected from the group consisting of pyridine, collidine, lutidine, picoline and acetonitrile, dioxane, tetrahydrofurane, N,N-dimethylformamide and a mixture of pyridine and tetrahydrofurane.

6. A process of claim 5, wherein the organic solvent is pyridine.

7. A process according to claim 1 wherein the reaction is carried out under a nitrogen atmosphere.

8. A process according to claim 1 wherein the reaction is carried out at a temperature between 75 and 110° C.

9. A process for the preparation of simvastatin or derivatives or analogs thereof, comprising a preparation process as defined in claim 1.

10. A process of claim 1 wherein the compound prepared is 6(R)-[2-(8'(S)-2'',2''-dimethylbutyryloxy-2'(S),6'(R)-dimethyl-1',2',6',7',8',8a-(R)-hexahydronaphthyl-1'(S))ethyl]-4(R) (dimethyl-terc-butylsiloxy)-3,4,5,6-tetrahydro-2H-pyran-2-one;

wherein lithium chloride is used as halide of formula $KX_n$;

wherein the organic solvent is pyridine;

wherein the reaction is carried out under a nitrogen atmosphere;

wherein the reaction is carried out between 75 and 110° C.; and wherein the process is for the preparation of simvastatin or derivatives or analogs thereof.

* * * * *

UNITED STATES PATENT AND TRADEMARK OFFICE
CERTIFICATE OF CORRECTION

PATENT NO. : 6,384,238 B1
DATED : May 7, 2002
INVENTOR(S) : Marco Zlicar

It is certified that error appears in the above-identified patent and that said Letters Patent is hereby corrected as shown below:

Column 9,
Line 20, replace "three" with -- ten --.

Signed and Sealed this

Twenty-sixth Day of November, 2002

*Attest:*

JAMES E. ROGAN
*Attesting Officer*   *Director of the United States Patent and Trademark Office*